United States Patent [19]

Trotel

[11] Patent Number: 5,022,060
[45] Date of Patent: Jun. 4, 1991

[54] HIGH ACQUISITION RATE TOMOGRAPHY BY TRANSLATIONAL STEP ROTATION

[75] Inventor: Jacques Trotel, Palaiseau, France

[73] Assignee: General Electric CGR SA, Issy les Moulineaux, France

[21] Appl. No.: 346,599

[22] Filed: May 2, 1989

[30] Foreign Application Priority Data

May 6, 1988 [FR] France ............................ 88 06138

[51] Int. Cl.$^5$ .............................................. A61B 6/00
[52] U.S. Cl. ........................................ 378/19; 378/196; 378/197
[58] Field of Search ............... 378/19, 4, 20, 24, 25, 378/26, 186, 197, 181

[56] References Cited

U.S. PATENT DOCUMENTS

| | | | |
|---|---|---|---|
| 3,121,793 | 2/1964 | Thomas | 378/197 |
| 3,803,417 | 4/1974 | Kok | 378/196 |
| 4,063,097 | 12/1977 | Barett et al. | 250/360 |
| 4,071,769 | 1/1978 | Brunnett et al. | 378/197 |
| 4,174,481 | 11/1979 | Liebetruth | 378/20 |
| 4,358,856 | 11/1982 | Stivender et al. | 378/197 |
| 4,363,128 | 12/1982 | Grady et al. | 378/181 |
| 4,630,202 | 12/1986 | Mori | 378/15 |
| 4,754,468 | 6/1988 | Mori | 378/19 |
| 4,829,547 | 5/1989 | Mustain | 378/197 |

FOREIGN PATENT DOCUMENTS 24028 2/1981 European Pat. Off. .
51350 5/1982 European Pat. Off. .

Primary Examiner—Edward P. Westin
Assistant Examiner—Kim-Kwok Chu
Attorney, Agent, or Firm—Oblon, Spivak, McClelland, Maier & Neustadt

[57] ABSTRACT

Problems related to acquistion time with reconstructed image type tomographs are resolved by causing step by step rotations of the X-ray tube/multiple detector set of this tomograph and, at each step, by causing a translational movement of this set in order to scan the entire region to be examined of a body under examination. It is shown that, by using a multiple row multidetector, it is possible, at equal speeds, to improve the quality of the images produced or, at equal quality, to increase the acquisition speed. Furthermore, this mode of operation is especially well suited to the monitoring of radiotherapy action where the practitioner, when acquiring images, needs to be able to touch the patient.

13 Claims, 4 Drawing Sheets

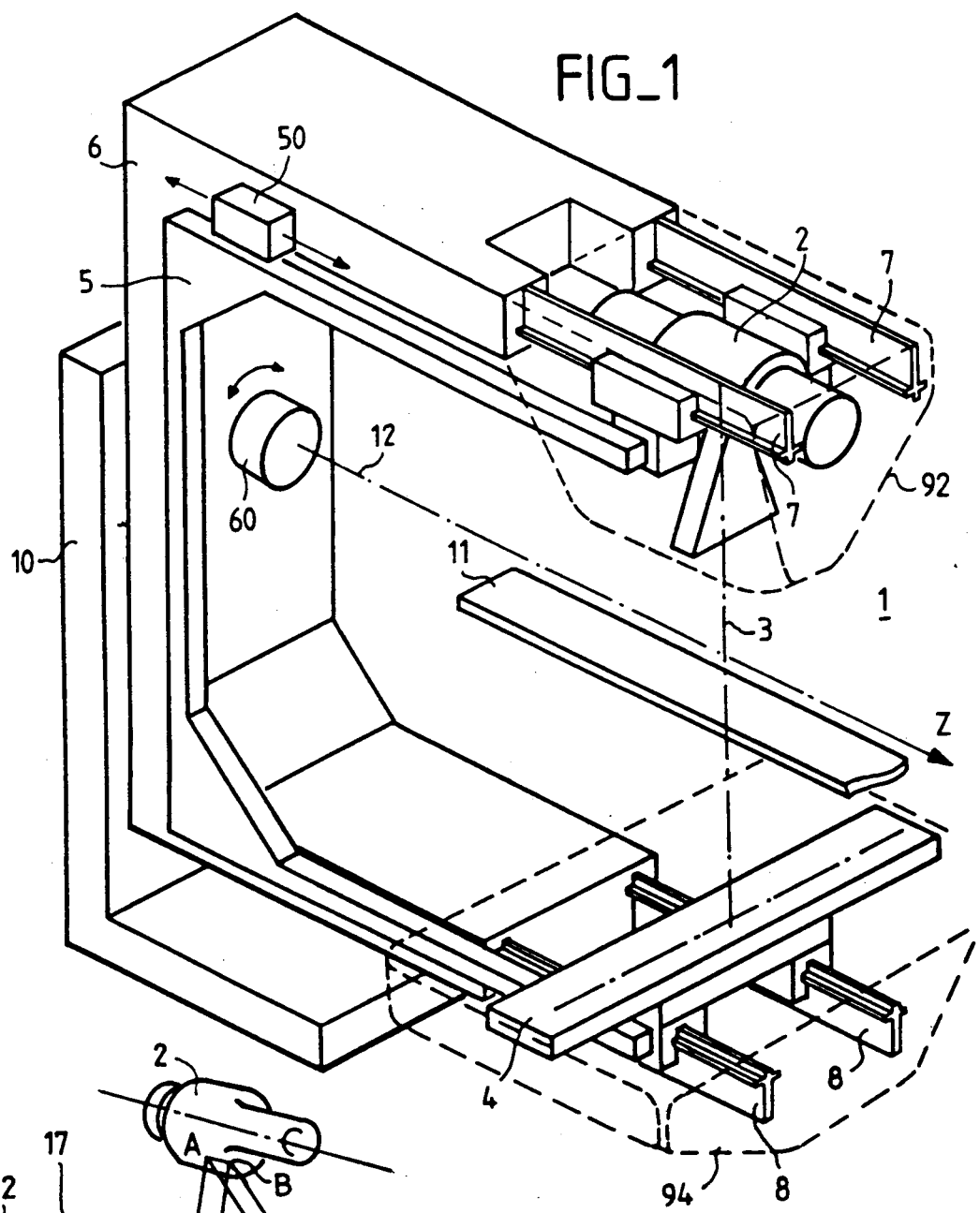
FIG_1
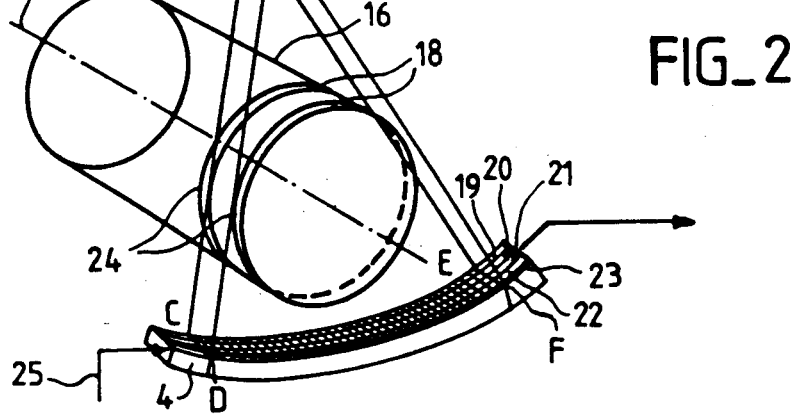
FIG_2

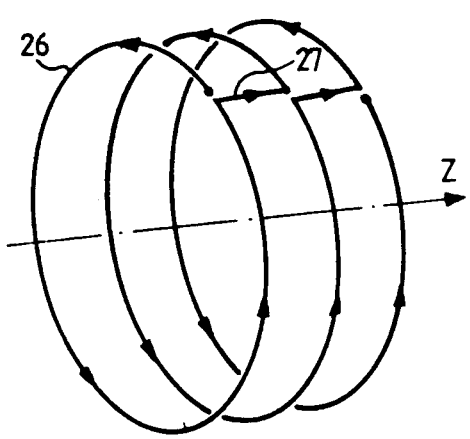
FIG_3-a
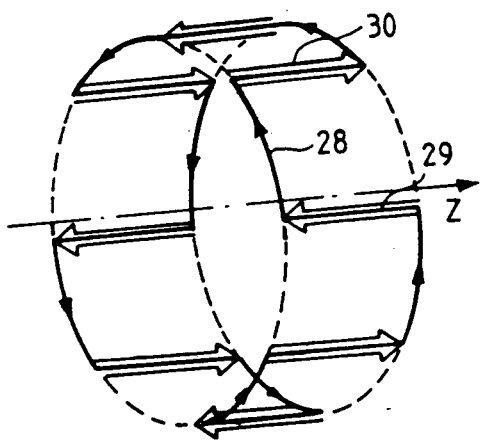
FIG_3-b
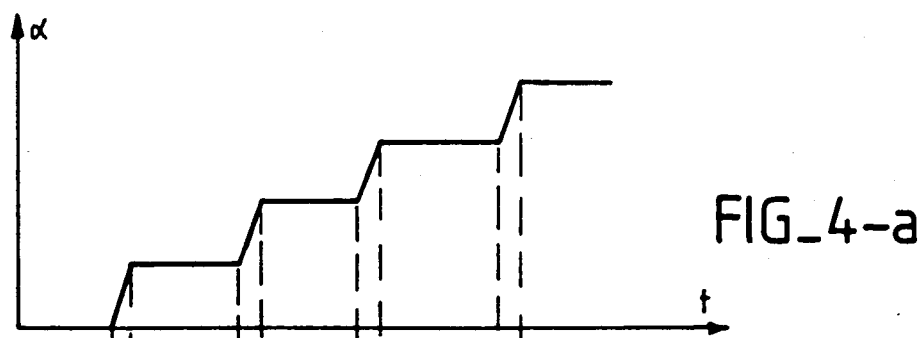
FIG_4-a
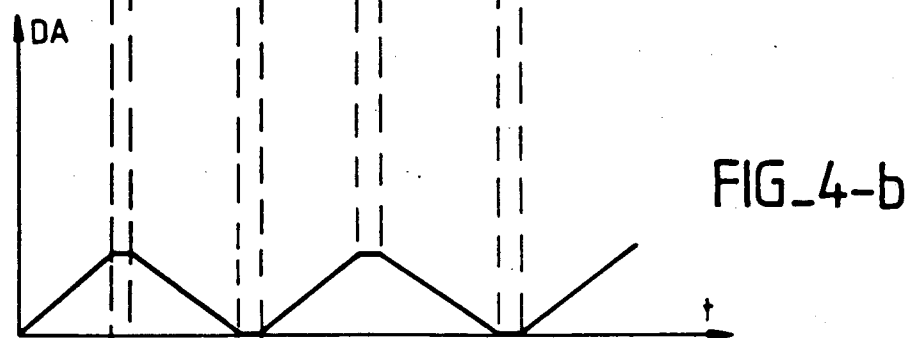
FIG_4-b
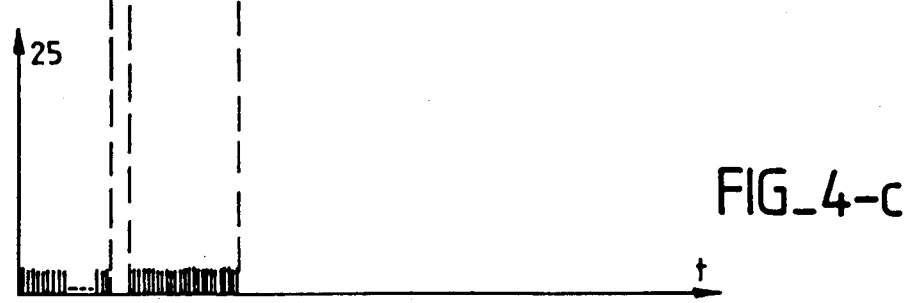
FIG_4-c

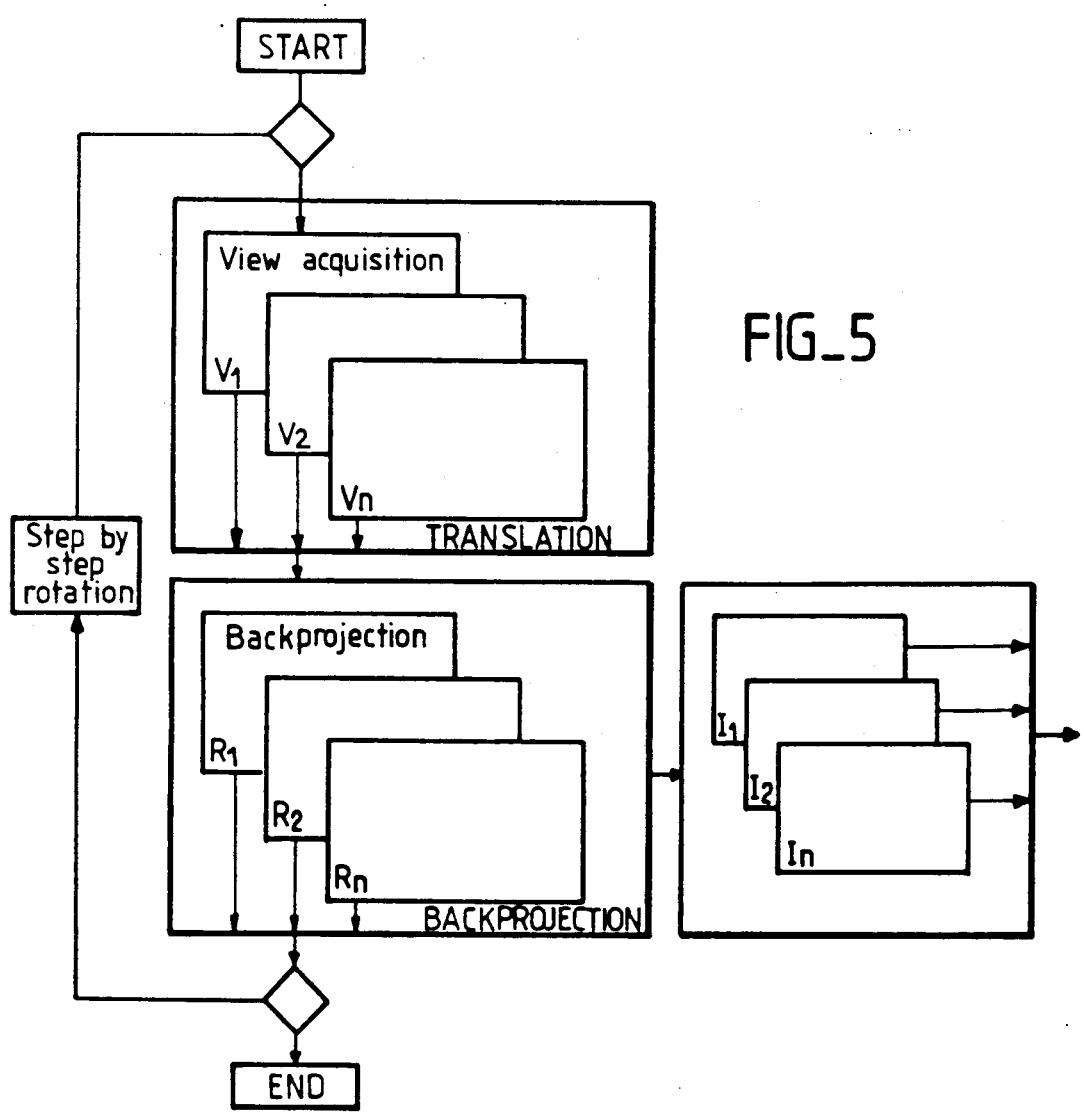
FIG_5
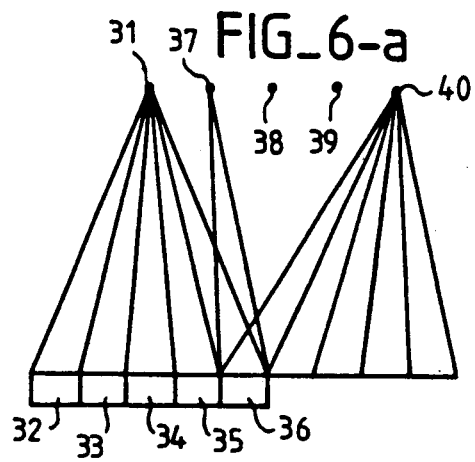
FIG_6-a
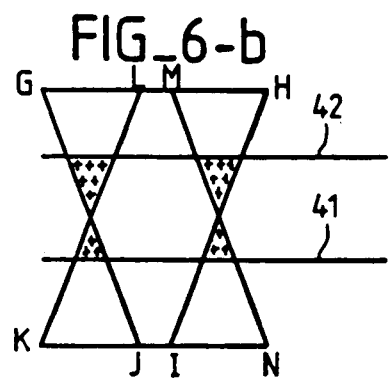
FIG_6-b

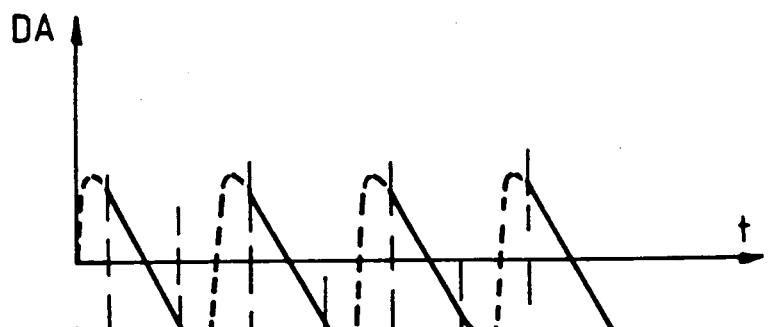
FIG_7-a
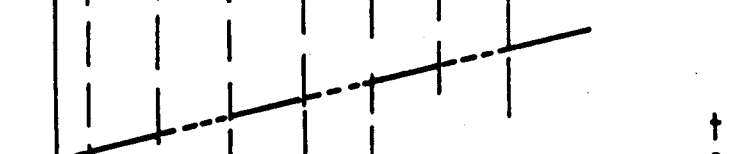
FIG_7-b
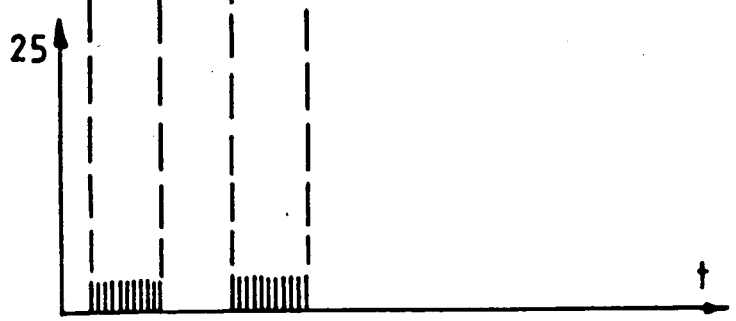
FIG_7-c

HIGH ACQUISITION RATE TOMOGRAPHY BY TRANSLATIONAL STEP ROTATION

BACKGROUND OF THE INVENTION

1. Field of the Invention

The present invention relates to a tomography device and process with a high acquisition rate, which can be used especially in medicine.

It relates generally to reconstructed image tomographs using digital processing of acquired data. The main purpose of the invention is to reduce the waiting time, especially for patients, entailed by the acquisition of multiple-section mode images or 3D images. The invention is also designed as a complementary installation for radiotherapy simulation machines. For machines of this type, the main constraint lies in the need to enable the practitioner to reach any organ of a patient at any moment, even during the tomography acquisition stage.

2. Brief Description of the Prior Art

There are known methods for reconstructed image tomographs wherein a set comprising a multidetector and an X-ray tube, fixed with respect to each other in the same plane, is used to acquire data relating to the image of a section, along this plane, of an object interposed between this X-ray tube and this multidetector. As a matter of fact, for each orientation of a particular direction of a fan beam radiation from the X-ray tube with respect to the object, it is possible to acquire a set of data representing a view of a slice of this object along this orientation. By repeating the experiment for different orientations, it is possible to acquire a set of views from which, under certain circumstances, a processing algorithm, commonly called a back projection algorithm, can be used to reconstruct the image of the section of the object along this plane.

The total time for acquisition of the data that enables the reconstruction of this image depends on the rotation speed of the multiple detector/X-ray tube set, the power of the X-ray tube and the sensitivity of the detector. Intuitively, it can be understood that the greater the power of the X-ray tube, the more it will emit X-rays of a given hardness (and not harder X-rays), the easier it will be to detect the residue of these rays, with the multidetector, after they have passed through the regions of the object, including the most opaque regions. It will then be possible to make the tube/detector set rotate more quickly to acquire the image more quickly. Following the same line of thought, the more sensitive the detector, the greater its quantum rate, and the more it is possible to increase its acquisition speed. This being the case, for a given technology of the X-ray tube/multiple detector set, the rotation speed of the set is a determining factor in the quality of the reconstructed image. For the lower the speed, the more possible it is to leave the multiple detectors under prolonged influence of the X-ray tube at each view, and the more precise and typical will be the data delivered by each of the cells of this detector. By contrast, the faster the operation, the more the image will deteriorate in terms of precision or resolution.

Currently available reconstructed image tomography machines are mainly so-called third generation machines. In these machines, the X-ray tube/multiple detector set, although it rotates, is connected by cables to the supply and receiving circuits of the machine. An acquisition then requires the acceleration of the X-ray tube/multiple detector set when starting up, the stabilizing, in speed, of this set, the acquisition proper of data at a stabilized speed, and the slowing down and then the stoppage of set (before the cable connections are pulled out). All this movement in rotation means that the set must perform two rotations on itself. For another acquisition, for the image of a section adjacent to a previously acquired section, this set of operations is started again, making the machine rotate in the other direction, and so on. In this operating mode, the result is that the acquisition time, in practice, is not related solely to the abovementioned choices as regards image quality but is related above all to this type of operation. In practice, the duration itself of acquisition varies from between half a second for images requiring low resolution up to ten seconds for images with fine resolution. In both cases, the acquisition of data relating to a section, taking acceleration and slowing down into account, is about 10 seconds.

The most commonly known multiple detectors are gas multiple detectors comprising a set of cells filled with gas (generally Xenon). Each cell of the multidetector has two metallic plates which are electrically biased at reverse voltages with respect to each other. The X-radiation, which goes through the object, causes this gas to be ionized and allows a leakage current to flow between the two plates biased at opposite high voltages. By measuring these leakage currents, it is possible to detect the data needed to reconstruct the image. A multidetector therefore has a great number of cells of the same type, aligned behind one another in a row, the main direction of which is contained in the section plane of the X-ray tube/multiple detector set. Cells of this type have a width of about 1.5 cm., measured perpendicularly to this sectional plane. So as to acquire the finest possible images, a collimator is used, the purpose of which is to reduce the omnidirectional radiation of the tube to radiation in a flat, fan-shaped beam which illuminates the entire detector and has a width corresponding to the resolution pitch, in terms of thickness, of the section to be reconstructed. In practice, this thickness may vary, from one machine to another, from 1 mm to 10 mm. When this thickness is equal to 10 mm, the delivery rate of the X-rays to the multidetector can reach a sensitive level more quickly, even for the most opaque regions of the object, so that such images, which are the poorest ones in terms of resolution, are, however, the most swiftly acquired images.

When it is sought to make a 3D depiction of the objects studied, images of several adjacent sections of this object are made. This is obtained by shifting the object, after making each section, along an axis perpendicular to the plane of the section with a length equal to the thickness of the beam. In one example, if 3D knowledge of an object is sought, along a length of 25 cm of this object with a resolution of 1 mm in the direction of this length, 250 adjacent sections have to be made. For medium resolution, the rotation (acceleration, stabilization, acquisition and slowing down) period, including the 1-mm lateral translations each image, may be about 4 seconds. The total acquisition time is then about 1000 seconds.

The tube/detector set thus described, taking into account the number of rotations to be made at each acquisition, should be contained in a fixed, circular cowl that prevents operators working on this machine from being injured. The various sections are acquired by shifting this cowl with respect to an examination bed on which the object (namely the patient, in medicine) is placed. In practice, the cowl is fixed to the ground and the bed moves by longitudinal translation in the machine. A circular cowl of this type does not give the practitioner access at all times to all the organs of a patient. For example, if the patient undergoes an examination in the region of the heart, his head is on one side of the machine while the lower part of the trunk and the lower limbs are on the other side. This disadvantage is particularly troublesome if the tomograph is used in a machine known as an radiotherapy simulator.

The purpose of a machine of this kind is to give data about the internal and external anatomy of a patient in order to determine, in advance, the characteristics of the beams which will be used when this patient is subsequently placed in a radiotherapy machine, so that the X-rays are given in the required dose to the regions that have to be treated and in the smallest possible dose to the other parts of this patient.

For examination using the radiotherapy simulator, the patient should be placed in the exact position that he would take in the radiotherapy machine. These positions are codified to give the maximum efficiency to the treatment. They are often incompatible with the geometry of conventional tomography machines, all the more so as the operator has to help the patient take these positions. Furthermore, during the examination using the simulator, the operator has to draw marks on the patient's skin to enable the positioning of the radiotherapy beams. This means that the neighbourhood of the patient should be easily accessible during the examination in the simulator.

Nor does removing the cowl, which is itself bulky, solve the problem for, when this cowl is not there, the operators and the patient run the risk of being caught up in the machine. To prevent this risky situation, speed limits have been laid down by the authorities. The purpose of these limits is restrict movements, without cowls, in such a way that source/multiple detector cannot make more than one rotation on itself in less than 60 seconds. Thus, the acquisition of tomographies in order to reconstruct a 3D depiction of an object is inconceivable.

In the invention, these drawbacks are coped with through the realization that, when the number of sections required is great (and especially when the longitudinal resolution required is high), the use of reconstructed image tomographs, as stipulated until now, has not been the most efficient one. Rather than acquiring each image through a group of views obtained by a rotation of the set around the object, and rather than causing each acquisition to be followed by an elementary translation to acquire a following image, the idea, on the contrary, is to cause a longitudinal scan of the object by the tube/detector set, and to cause each translation to be followed by a one-step rotation. At each rotational step, the object is explored by a longitudinal scan. Preferably, in an improvement, the scanning is done downwards (in the head-to-foot direction) and then upwards (in the foot-to-head direction) at the following rotation step and so on.

The comparative magnitudes are as follows: in the prior art, 250 images each comprising 1000 views and each lasting four seconds, including the translation between images, resulted in a total acquisition time of 1000 seconds. With the method of the invention, the procedure comprises a corresponding number of 000 translations, each followed by a rotational movement of one step by the X-ray tube/multiple detector set. It should be noted that these step-by-step rotational movements have very small amplitude; they can therefore be very fast. In fact, their amplitude is about 18 angular minutes (to 1 angular degree depending on the quality of the examination). Their fast execution cannot entail any risk to operators close to the machine. Similarly translations along about 30 cm (25 cm of exploration and twice 2.5 cm of acceleration and slowing down on either side) can also be fast. Thus, it is possible to achieve a total acquisition time of 1000 seconds. However, in this case, the method according to the invention has the advantage wherein, since the accelerations and slowing down of the set are relatively not as long, the relative time taken for the use of the multidetector for detection purposes may be lengthier. Finally, the sensitivity of the machine is thereby increased. For example if the longitudinal scanning time is about 0.75 seconds for 25 cm, the radiation time of the multidetector with respect to a one-millimeter thick slice is about 3 milliseconds (0.750/250). By comparison, for third generation machines, either this using time is shorter in order to keep the total acquisition time to the same length, or this intrinsic using time is the same but, in this case, the total acquisition time is longer.

Moreover, in an improvement, these results, which are again partly comparable, can be considerably increased in the invention if the multidetector is of the multiple row type. For, it is possible to choose a multidetector of the type described in the European patent No. 0 051 350 filed on 28th July 1981.

This multidetector has a two-dimensional array of detecting cells. In this case, the processing is of the discrete type. During the translation, the electrical charges, representing data from the cells of one of the rows of the multiple row multidetector, are transferred to adjacent cells of an adjacent row in the reverse direction to the translation movement. The data content of the cells of the last row takes into account the integration effect resulting from these transfers. It is used as being typical of the view.

To simplify the description, it may be indicated that, beneath a given slice of the object, there is a flow, in order, owing to the movement, of the rows of cells numbered 1 to n (n being equal, for example, to 5). Each time that another row is placed under the slice, the data content of the cells of the previous row is transferred into the cells of this row, and so on until the row number n of the cells is under the slice. At the end of the irradiation of this row beneath this slice, the signal is sampled. This method has the advantage, finally, of subjecting the examined slice to radiation which is n times longer. The immediate result of this is that, for equal resolution quality, the image can then be acquired n times faster; or else at equal acquisition speed, its resolution may be n times better.

Moreover, the device according to the invention wholly complies with the legal requirements referred to above. For, at each rotation by a small angle, of a fraction of a degree, there is no reason to take too many precautions. The motion can therefore be very swift because it has, moreover, a very small span. Besides, the translational movements, of about 30 cm, can be done inside a cowl. In fact, on 30 cm, an operator could be injured if he were caught up by the machine. But since, in the invention, complete rotations are no longer done as in third generation machines, it is no longer necessary to create a circular type of structure for this cowl. A structure with a general shape of an arc of a circle would be enough. Through the inside of the arc of the circle it then becomes possible to reach all the organs of the patient.

SUMMARY OF THE INVENTION

An object of the invention, therefore, is a tomography device comprising:

an X-ray tube/multiple detector set provided with an X-ray tube arranged so as to emit radiation towards a multidetector with which it is mechanically associated, rotating means to make the set rotate on an axis of rotation said axis passing transversally between the tube and the multidetector, a resulting rotation angle of said set having a minimum exploration angular value so necessary for the reconstruction of an object placed between said tube and said multidetector translation means to cause at least said multidetector to move along this axis of rotation, a length of this translation corresponding at least to a length of a region to be examined of said object means to process signals given by the multidetector in order to produce images of the interposed object the rotation means comprise means to make the set rotate by an angle at least equal to said minimum angle in such a manner that a mean tangential speed of said multidetector be less quick than a translation speed of said multidetector and, as a result, that the duration of the total rotation duration of said set be greater than the necessary duration for the multidetector to translate at least one time over the entire length to be examined, and means to make the tube transmit during the translation displacement.

BRIEF DESCRIPTION OF THE DRAWINGS

The invention will be better understood from the following description and the appended figures. These figures are given purely as an indication and in no way restrict the scope of the invention. Of these figures:

FIG. 1 shows a tomography device according to the invention;

FIG. 2 shows a detail of the device of FIG. 1 depicting the special features of the operation of a multiple row multidetector;

FIGS. 3a and 3b give a comparison of the exploration modes in the prior art and according to the invention respectively;

FIGS. 4a to 4c are timing diagrams of signals playing a part in the control of the driving means and in the control of the detection means of the device according to the invention;

FIG. 5 shows a specific feature of the acquisition and reconstruction mode according to the invention;

FIGS. 6a and 6b are indications that enable the modification of the reconstruction algorithms according to a recommended acquisition mode;

FIG. 7 shows an alternative of the timing diagrams of FIGS. 4a to 4c.

DESCRIPTION OF PREFERRED EMBODIMENTS

FIG. 1 shows a tomography device according to the invention. This device has an X-ray tube/multiple detector set 1. This set is the gathering of such an X-ray tube and of a multidetector. In this set, an X-ray tube 2 radiates an X-radiation 3 towards a multidetector 4 with which it is mechanically associated. For example the tube 3 and the multidetector 4 are schematically associated by a linking structure 5 so that they undergo movement together: the X-radiation being always pointed accurately towards the multidetector 4. The set 1 is mounted in a hoop 6 which has the general shape of an arc of a circle. This hoop 6 is connected to a column base 10 by a bearing which enables a rotation of this hoop 6 with respect to an axis 12 perpendicular to an X-ray beam 3. The set 1 and the structure 5 are mounted on the hoop 6 by means of slides 7 and 8 which give the set 1 a translation movement parallel to the axis 12 in a Z direction. Motors 50 and 60 respectively give the linking structure 5 a translation movement parallel to the axis 12, and the hoop 6 a rotational movement about the axis 12.

A patient or an object to be examined are placed on a table 11 which is substantially parallel to the axis 12 and is designed to be interposed in the path of the X-radiation 3. This mechanism is used as means to make the tube/multiple detector set rotate on the axis 12, pointed in a direction parallel to a panel 11. The tube 2 and the multidetector 4 are respectively contained in cowls 92 and 94 shown with dashes. The cowls 92 and 94 are fixed to the hoop 6. They provide clearance in their internal volume, useful in the translation of the tube and the multidetector.

With the rotation means, the device of the invention also has, conventionally, translation means to move this set in a Z direction along the axis 12 with respect to the panel 11. In practice, the panel 11 can be shifted longitudinally and vertically. Circuits (not shown) placed for example in the column base 10 are used to pick up and process the signal delivered by the multidetector 4 in order to produce and display images of sections of objects interposed, on the panel 11, in the path of the radiation 3.

The essential characteristic of the invention lies in its use. To obtain a set of tomographies, the set 1 including its cowls 92 and 94, are shifted step by step in rotation and; At each step, while this set 1 is kept fixed in rotation, it is made to translate along the axis 12 passing through its center of rotation. In this way, an entire corresponding portion to be examined of the object is scanned. This translation movement does not take place by shifting either the panel 11 or the cowls 92 and 94. For, as indicated earlier, this shift is quite large and should be about 30 cm. Moreover, since it should be quite swift to enable the quick acquisition of all the images, this shifting of the set 1 preferably takes place inside cowls 92 and 94 fixed with respect to the hoop 6. For this purpose, the linking structure 5 is, for example, of a lattice type and may be driven in translation by motors such as 50 in one direction and then in another direction at a following rotational step. The motors such as 50 may be of all types: electrical, pneumatic etc. They may also be replaced by independent motors placed directly on the tube 2 and the multidetector 4 and automatically locked in position with respect to each other in order to permanently provide efficient radiation of the multidetector 4 by the X-rays 3. In this latter case, the structure 5 may be removed.

In view of the problems of inertia which may arise owing to the fragility of this lattice structure 5, or quite simply because of the weight of the multidetector 4 and the tube 2, there may be problems related to radiation faults. However, in the invention, to remove this problem and, above all, to enable an increase, while maintaining constant quality, of the acquisition rate, a multidetector is made of the type described in the above mentioned European patent or, again, in a non-discrete mode, of the type described by FRANCK A. di BIANCA in "Kinestatic Charge Detection", MED. PHYS. 12(3), May-June 1985, pages 339-343. This article provides for the integration of the signals by a drift of ions in a gas detector. This drift is in reverse to the scanning motion. The acquisition mode thus recommended with integration makes the longitudinal resolution of the acquisition dependent, no longer on the accuracy of a collimator present between the X-ray tube and the multidetector, but on the mode for the sampling and integration of the signals delivered by a multidetector of this type. This multidetector becomes one that can be likened to a multiple row multidetector. The rows are parallel to one another and substantially perpendicular to the direction of movement. The result of this is that acquisition distortions, due to different inertial charges when the translation is started, can be ignored if attention is paid solely to the precise identifying of the position of the multidetector 4 in the cowl 94 at the sampling moment. It is thus possible to choose a wide collimator while at the same time not damaging the quality of the longitudinal resolution.

It will be seen in FIG. 1 that the shapes of the hoop 6 and the cowls 92 and 94 make it possible to reach all the organs of the patient on the table 11 at all times. This is an important feature for application to a radiotherapy simulator as indicated above. This feature is more usually suitable for examinations where the patient does not have to take a position compatible with a conventional instrument and for examinations requiring the help of an operator or the presence of bulky but indispensable accessory equipment as in certain traumatological examinations.

FIG. 2 is used to explain the operation of the multiple row multidetector. It gives a schematic view of the movement of the tube 2 and the multidetector 4 with respect to a body 6 placed, on the whole, along the axis 12 of the machine. It is assumed, first of all, that the tube 2 emits a fan-shaped X-radiation 3 along the contour ABCDEF of a parallel type in a slice 18. It may be assumed, during the movement of the set 1 towards the rear 17 of the object !6, that each irradiated slice 18 of this object, the radiological absorption signal of which is picked up by the multiple row multidetector 4, can be divided into a number n of elementary slices each corresponding to one of the rows of the multiple row multidetector. For example, in FIG. 2, the multiple row multidetector 4 has five rows marked 19 to 23. At a given instant, the multidetector is placed under the slice 18. At a following instant, when the irradiated slice 18 becomes the slice 24 which partly inter-penetrates the slice 18, a large part of this slice 18 continues to undergo radiation. However, for that part of this slice 18 where the radiological absorption signal reached the row 19 of the multiple row multidetector, the signal now reaches the row 20 while the radiological absorption signal which reached the row 20 now reaches the row 21 and so on.

Before the tube 2 and the multidetector 4 are shifted a little further towards the rear 17 of the body 16, it is necessary to pick up the signal available in the row 23. A rate-setting command 25, applied to the multiple row multidetector 4, is used to transfer, at each rate pulse, the electrical charges from the cells of each row into the corresponding cells of a row which is adjacent, but in a direction opposite to the direction of the movement. The rate-setting command 25 also enables the sampling of the signal given by the last row 23 of the multidetector 4. The transfer of the electrical charges from one cell to another, in a discrete case or along a gas cell by continuous drift of ions, as described in the above article, is quite capable of being transposed to the invention. The setting of the rate it possible to organize this transfer as well as provides for the sampling in the last row, of the useful data. In the discrete example, at each rate pulse, the data content of a cell replaces the content of the adjacent cell. The cells of the row of the scan driving edge are reset at each pulse.

FIGS. 3a and 3b give a comparative view of the acquisition modes in the prior art and in the invention respectively. In the prior art, an image was acquired when the X-ray tube/multiple detector set made rotations on itself, such as the rotation 26. After each rotation, a slight translational motion 27 placed the set vertical to another section of the body to be examined. In the invention (FIG. 3b), the hoop 6 is subjected to slight step-by-step rotations 28 (shown in a exaggerated way herein) and, between each step, inside the cowls 92 and 94, the X-ray tube 2/multiple detector 4 set is subjected to translational motions such as 29.

In a preferred way, with a charge transfer and bi-directional multiple row multidetector (namely one capable of transferring charges in one direction and, by quick modifications, in an opposite direction), after each rotation by one step 28, the translational movement has an the opposite direction, inside the cowls 92 and 94, in the direction 29 of a previous shift.

FIGS. 4a to 4c respectively show the rotational steps $\alpha$, in time, of the cowls 92 and 94, the alternating shifts DA of the set 1 in the cowls as well as the rate-setting commands 25. For the duration of an acquisition, during a first period, the cowls are fixed ($\alpha$ does not vary), the shift is linear (DA follows a regular slope) and the number of commands 25 corresponds substantially to the number of slices to be acquired throughout the scanning period. This number also corresponds to the longitudinal resolution to be obtained. For example, on 250 mm, with a resolution of 1 mm, there are 250 rate-setting pulses 25.

If the detector is not bi-directional, the preferred embodiment corresponds to FIG. 7, namely to a continuous rotation and to an asymmetrical motion of translation. This asymmetrical motion comprises a slow movement during acquisition in a direction tolerated by the detector and a fast return movement in a direction where the detector is inactive.

FIG. 5 shows a special feature of the mode for acquiring and reconstructing images obtained according to the invention. For, in the prior art, the acquisition of a view $V_1$ is usually followed, conventionally, by a back projection $R_1$, used to define a corresponding image $I_1$ in a first stage. When the tomograph rotates on itself, it then acquires views $V'_1$ then $V''_1$ ... which are transformed by back projection operations $R'_1$ then $R''_1$ ... in order to complete the definition of the image $I_1$. When the image $I_1$ is completely defined, the tomograph of the prior art is translated (27) vertical to the following slice and the process is started again.

In the invention, the usable back projection algorithm will be the same. Quite simply, between the acquisition of one view $V_1$ and the acquisition of the following view $V'_1$, corresponding to one and the same slice in the object, the scanning translation 29 will have given sections $V_2 \ldots V_N$ which are respectively subjected to back projections $R_2 \ldots R_N$ in order to define, in a first phase, the other images $I_2 \ldots I_N$ (in the example, N equals 250). The consequence of this situation is that, in practice, the memory capacities and the processing algorithms are the same. Only the organization of the acquisition changes correspondingly.

In the example described where, from one translation 29 to another 30, the direction in which the object 16 is explored is reversed, it is necessary, knowing that the view $V'_N$ is then acquired before the view $V'_1$, to perform the back projections $R_N \ldots R_1$ in the appropriate order to complete the definition at a subsequent run of the images $I_N \ldots I_1$.

FIG. 2 shows an ideal type of radiation in which the X-radiation source is not localized but extends over a distance AB, and wherein the radiation is of a parallel type. The reality is different, and the X-ray source is localized. FIG. 6a shows that part of the examined body which is actually irradiated and taken into account during a translational movement. The figure shows a first position 31 of the X-ray focal spot as well as an alignment of cells 32 to 36 belonging, for example, to the rows 19 to 23 respectively of the multiple row multidetector of FIG. 2. Whenever the X-ray source moves towards an adjacent position, for example the positions 37 to 40, the electrical contents of the cells 36 to 32 is shifted in reverse direction, namely from the cell 36 towards the cell 32.

It is seen that, when the X-ray tube is at 31, the zone of the irradiated object, for which the measurement of radiation is detected by the cell 36, is contained in the triangle coming from the source 31 and reaching this cell 36. When the source has shifted to 37, the cell 36 has shifted rightwards and the cell 35 has come to take the place of the cell 36 in the same vertical line with respect to the examined body. This cell 35 then receives a radiological absorption signal corresponding to what has occurred in the triangle, which has its vertex at 37 and its base also at 36. Furthermore, owing to the transfer, the content of the electrical charges of the cell 36 has been transferred to the cell 35 causing the integration phenomenon that favors the increase in sensitivity obtained by the invention. And so on until the tube takes up the position 40 and the cell 32 is placed at the position where the cell 36 currently is placed in the drawing.

The result of this is that, in these conditions, the examined part of the body is not a perfectly plane slice as would be suggested by the slice 18 of FIG. 2 but is, on the contrary, a slice with a trapezoidal section, the large base of which is equal to the width of the multiple row multidetector and the small base of which is equal to the width of one of the rows of the multiple row multidetector. From this, it can be deduced that it is not possible, in these circumstances, to use a multiple row detector with too many rows and an excessively large detector. A number of rows equal to five would appear to be a suitable compromise from this point of view.

In practice, this adverse phenomenon is somewhat attenuated because the body 2 is not placed in direct contact with the X-ray tube on the one hand and the multidetector on the other. It occupies an intermediate position. In FIG. 6b, the intermediate position of the body is shown between the straight lines 41 and 42 while the exploration trapezoids, GHIJ and KLMN respectively, are present. These back-to-front trapezoids correspond to surfaces of slices irradiated when the X-ray tube is in a given position (the position of FIG. 1 for example) and in a position which is symmetrical (with reference to the axis 12) to this given position. It will be seen that regions of the object shown with small crosses are irradiated to contribute to a view along a given direction while they are not irradiated to contribute to a view which is symmetrical, in its orientation, to the view in question.

To begin with, this type of theoretical fault may be ignored and it is possible to reconstruct the images as if the radiation were of a perfectly parallel type. Furthermore, it is possible to envisage an operating mode where the X-ray source 2 does not undergo any translation movement parallel to the axis 12 but only a rotational movement. To this end, the detector with its translational motion gives each angular position the data corresponding to a conical projection of the object. It may be shown that a set of conical projections, corresponding to a circular movement of the source, does not enable a totally rigorous reconstruction of the object. A more complex movement of the source is needed. However a circular movement gives an approximate reconstruction. Reconstruction algorithms from conical projections are available. They are complex and require high computing power, but in a simplified form in a case where the source describes only a circular movement, the invention is easily applicable.

What is claimed is:

1. A tomography device comprising:
   an X-ray tube/multiple detector set provided with an X-ray tube arranged so as to emit radiation towards a multidetector with which it is mechanically associated,
   rotating means to make the set rotate on an axis of rotation said axis passing transversally between the tube and the multidetector, a resulting rotation angle of said set having an exploration angular value so necessary for the reconstruction of an image of an object placed between said tube and said multidetector
   translation means to cause at least said multidetector to move along this axis of rotation, a length of this translation corresponding to least to a length of a region to be examined of said object
   means to process signals given by the multidetector in order to produce images of the interposed object
   the rotation means comprise means to make the set rotate a total angle equal to said exploration angular value in such a manner that a mean tangential speed of said multidetector be less than a translation speed of said multidetector and, as a result, that the duration of the total rotation of said set be greater than the necessary duration for the multidetector to translate at least one time over the entire length to be examined,
   and means to make the tube transmit during the translation displacement.

2. A tomography device comprising:
   an X-ray tube/multiple detector set provided with an X-ray tube arranged so as to emit radiation towards a multidetector with which it is mechanically associated,
   rotating means to make the set rotate on an axis of rotation passing between the tube and the multidetector,
   translation means to cause the set to move along this axis of rotation, means to process the signals given by the multidetector in order to produce images of objects interposed between the detector and the X ray tube, the rotation means comprise means to make the set rotate step by step, and the translation means comprise means to move the set in translation at each rotation step.

3. A device according interposed between the detector and the X-ray tube, to claim 1 wherein:

the multidetector is of the multiple row type and, the processing means comprise means to integrate, in time, signals given by this multiple row multidetector during the translational movement of the set.

4. A device according to either of the claims 1 or 2 wherein the translational means comprise means to shift the set in one direction and then in another direction from one rotation step to another.

5. A device according to either of the claims 1 or 2 wherein the means for associating the tube with the multidetector have the general shape of an open arc of a circle.

6. A device according to either of the claims 1 or 2 wherein the multidetector has multiple rows and is of the ion drift type.

7. A device according to either of the claims 1 or 2 wherein the multidetector has multiple rows and is of the type having a two-dimensional array of detecting cells.

8. A device according to claim 7 wherein the cells comprise charge transfer devices.

9. A device according to claim 7 wherein the multiple row multidetector has an array of photo-detector elements.

10. A tomography process comprising the following steps:

an X-ray tube/multiple detector set is provided with an X-ray tube arranged so as to emit radiation towards a multidetector with which it is mechanically associated, the set is made to rotate by rotating means on an axis of rotation, said axis of rotation passing transversally between the tube and the multidetector, a resulting rotation angle of said set having at least a minimum exploration angular value so necessary for the reconstruction of an object placed between said tube and said multidetector at least said multidetector is caused to move by translation means along this axis of rotation, a length of this translation corresponding at least to a length of a region to be examined of said object signals given by the multidetector are processed in order to produce images of the interposed object the rotation means comprise means to make the set rotate by said minimum angle in such a manner that a mean tangential speed of said multidetector be less quick than a translation speed of said multidetector and, as a result, that the duration of the total rotation duration of said set be greater than the necessary duration for the multidetector to translate at least one time over the entire length to be examined, and the tube is made to transmit during the translation displacement.

11. A process according to claim 10 wherein the set is made to rotate step by step.

12. A tomography device comprising:

an X-ray tube/multiple detector set provided with an X-ray tube arranged so as to emit radiation towards a multidetector with which it is mechanically associated, rotating means to make the set rotate on an axis of rotation said axis passing transversally between the tube and the multidetector, a resulting rotation angle of said set having an exploration angular value so necessary for the reconstruction of an image of an object placed between said tube and said multidetector translation means to cause at least said multidetector to move along this axis of rotation, a length of this translation corresponding to least to a length of a region to be examined of said object means to process signals given by the multidetector in order to produce images of the interposed object the rotation means comprise means to make the set rotate a total angle equal to said exploration angular value in such a manner that a mean tangential speed of said multidetector be less than a translation speed of said multidetector and, as a result, that the duration of the total rotation of said set be greater than the necessary duration for the multidetector to translate at least one time over the entire length to be examined, and means to make the tube transmit during the translation displacement wherein the tube and the multidetector are contained within cowls which are held fixed during the translational movement on the one hand and which is rotatively moved about said axis during the rotation on the other hand.

13. A tomography device comprising:

an X-ray tube/multiple detector set provided with an X-ray tube arranged so as to emit radiation towards a multidetector with which it si mechanically associated, rotating means to make the set rotate on an axis of rotation passing between the tube and the multidetector, translation means to cause the set to move along this axis of rotation, means to process the signals given by the multidetector in order to produce images of objects interposed between the detector and the X-ray tube, the rotation means comprise means to make the set rotate step by step, and the translation means comprise means to move the set in translation at each rotation step wherein the tube and the multidetector are contained within cowls which are held fixed during the translational movement on the one hand and which is rotatively moved about said axis during the rotation on the other hand.

* * * * *